(12) United States Patent
Groβ et al.

(10) Patent No.: US 7,985,023 B2
(45) Date of Patent: Jul. 26, 2011

(54) MEDICAL EXAMINATION DEVICE

(75) Inventors: Stefan Groβ, Trabitz (DE); Franz Schmeisser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 27 days.

(21) Appl. No.: 12/326,631

(22) Filed: Dec. 2, 2008

(65) Prior Publication Data

US 2009/0147924 A1 Jun. 11, 2009

(30) Foreign Application Priority Data

Dec. 7, 2007 (DE) .......................... 10 2007 058 990

(51) Int. Cl.
H05G 1/06 (2006.01)
H05G 1/02 (2006.01)

(52) U.S. Cl. ....................... 378/194; 378/197

(58) Field of Classification Search ............... 378/4–20, 378/101, 193, 194, 197, 204, 205, 210
See application file for complete search history.

(56) References Cited

U.S. PATENT DOCUMENTS

| | | | | |
|---|---|---|---|---|
| 2,093,411 A * | 9/1937 | Bowden et al. | ................. | 156/55 |
| 3,118,066 A * | 1/1964 | Thomas et al. | ................ | 378/194 |
| 3,121,793 A * | 2/1964 | Thomas | ........................... | 378/91 |
| 3,175,085 A * | 3/1965 | Avery | ........................... | 378/197 |
| 3,281,598 A * | 10/1966 | Hollstein | ....................... | 378/179 |
| 3,288,025 A * | 11/1966 | Litz et al. | ........................ | 355/41 |
| 3,373,285 A * | 3/1968 | Barrett | ......................... | 378/194 |
| 3,541,334 A * | 11/1970 | Sobolewski et al. | .......... | 378/194 |
| 3,722,263 A * | 3/1973 | Hautaniemi et al. | ............ | 73/622 |
| 3,902,070 A * | 8/1975 | Amor et al. | .................... | 378/194 |
| 4,020,348 A * | 4/1977 | Turcotte et al. | ........... | 250/363.08 |
| 4,041,320 A * | 8/1977 | Amor et al. | .................... | 378/194 |
| 4,063,104 A * | 12/1977 | Gadd | .............................. | 378/11 |
| 4,146,795 A * | 3/1979 | Braden et al. | ..................... | 378/4 |
| 4,901,339 A * | 2/1990 | Heinz et al. | .................... | 378/197 |
| 7,654,738 B2 * | 2/2010 | Fink et al. | ...................... | 378/194 |
| 2008/0037704 A1* | 2/2008 | Hoffmann | ....................... | 378/37 |
| 2008/0119714 A1* | 5/2008 | Meissner et al. | ............. | 600/407 |

FOREIGN PATENT DOCUMENTS

| | | |
|---|---|---|
| DE | 43 11 702 A1 | 10/1994 |
| DE | 102 37 873 B3 | 3/2004 |
| DE | 10 2005 053 030 A1 | 5/2007 |
| EP | 1 389 707 A2 | 2/2004 |

OTHER PUBLICATIONS

German Office Action dated Nov. 8, 2008 with English translation.

* cited by examiner

*Primary Examiner* — Anastasia Midkiff
(74) *Attorney, Agent, or Firm* — Lempia Summerfield Katz LLC

(57) ABSTRACT

A medical examination device is provided. At least some of the supply lines used to operate the examination device are routed from above to the examination device, with the supply lines being arranged on a gallows which is mounted rotatably on a rail-guided carriage and being attached to a longitudinal section by at least one Bowden cable arranged on the gallows.

13 Claims, 2 Drawing Sheets

MEDICAL EXAMINATION DEVICE

The present patent document claims the benefit of German Patent Application DE 10 2007 058 990.7 filed on Dec. 7, 2007, which is incorporated by reference.

BACKGROUND

The present embodiments relate to a medical examination device. More specifically, the present embodiments may relate to an x-ray device with at least some supply lines used to operate the examination device routed from above to the examination device.

Medical examination devices, such as x-ray devices, can be controlled by an operator or robots. The medical examination devices have supply lines that are routed from above, for example, from the ceiling, to the examination device, such that the supply lines are not damaged during the movement of the components of the examination device. The supply lines, which may be power or signal lines or compressed air or hydraulic supply lines of a radiation source or of a radiation detector or of a patient positioning couch. The examination device and/or all its moveable components are not restricted in terms of their freedom of movement. Accordingly, it is necessary to keep the cables as tight as possible and to avoid snagging and to provide for an adequate line reserve for the movements of the device components. The supply lines are affixed to one or more cable pulls mounted on the ceiling. The cable pulls pull the lines toward the ceiling. In respect of the several degrees of freedom of movement of various device components, which can be moved in any horizontal direction as well as vertically, such cable pulls which are mounted on the ceiling are too "rigid", and an overdimensioned line storage unit is consequently to be provided as a result.

SUMMARY AND DESCRIPTION

The present embodiments may obviate one or more of the drawbacks or limitations inherent in the related art. For example, in one embodiment, an examination device has an improvement in the way in which the supply lines are attached.

A medical examination device may include supply lines. The supply lines may be power or signal lines or compressed air or hydraulic supply lines of a radiation source or a radiation detector or a patient positioning couch. The supply lines may be arranged on a gallows that is rotatably mounted on a rail-guided carriage and to be attached to a longitudinal section by at least one Bowden cable on the gallows.

The supply lines and/or a tube in which all supply lines are routed may be attached to a Bowden cable, such as a cable pull. The cable pull may not be firmly positioned and may instead be moveable in a longitudinal manner both about a vertical axis and about at least one horizontal axis. The cable pull is positioned on a gallows. In other words, the cable pull may be positioned on an elongated bracket that essentially extends horizontally. The gallows may be arranged in a rotatable manner about a vertical axis on a rail-guided carriage which can be displaced along at least one horizontal axis. The attachment of the supply lines by the cable pull allows the supply lines to be held tight and to be positioned as close to the ceiling as possible, as is customary. The movement mechanism may allow for any freedom of movement of the device located therebelow. The line storage unit, such as the cable reserve or tube reserve, which is to be provided on the ceiling, may be kept appreciably shorter. As a result of the coupling with the horizontally moveable carriage, the short reserve is always carried along at the same time. The rotatable arrangement of the gallows, below which the line reserve is virtually embodied, also allows the line reserve to be included during a rotational movement, so that the maximum line reserve is available in each case and at each position, and can be kept sufficiently short.

The supply lines are arranged on the gallows and are connected by the gallows to the carriage. Accordingly, stationary feed lines may be decoupled. The stationary feed lines are arranged on the ceiling or rails and may be connected to the carriage or to the gallows in an energy chain. The feed lines may be routed in or along an energy chain. The energy chain may be a chain link guide. The energy chain may allow a path equalization in the direction of the carriage's direction of movement, in other words the feed lines. Accordingly, the feed lines may be coupled on the carriage or gallows to the corresponding supply lines, which are then routed to the examination device, are likewise mounted and carried along at the same time in a moveable fashion in the energy chain as far as is necessary. Because the energy chain is arranged on the ceiling or rails and/or is positioned in this region, they are completely outside any range of movement of any of the device components. The supply lines may be routed by the carriage into the energy chain. Accordingly, the supply lines are not separated on the carriage.

A balancing weight may be provided on the gallows. The balancing weight may counteract possible weight or center of gravity modifications, which result from a movement of the supply lines.

The supply lines may be accommodated in a common tube, such as a grooved tube, to which the Bowden cable attaches. The Bowden cable may be a cable pull or a chain pull.

DETAILED DESCRIPTION

Figure 1:
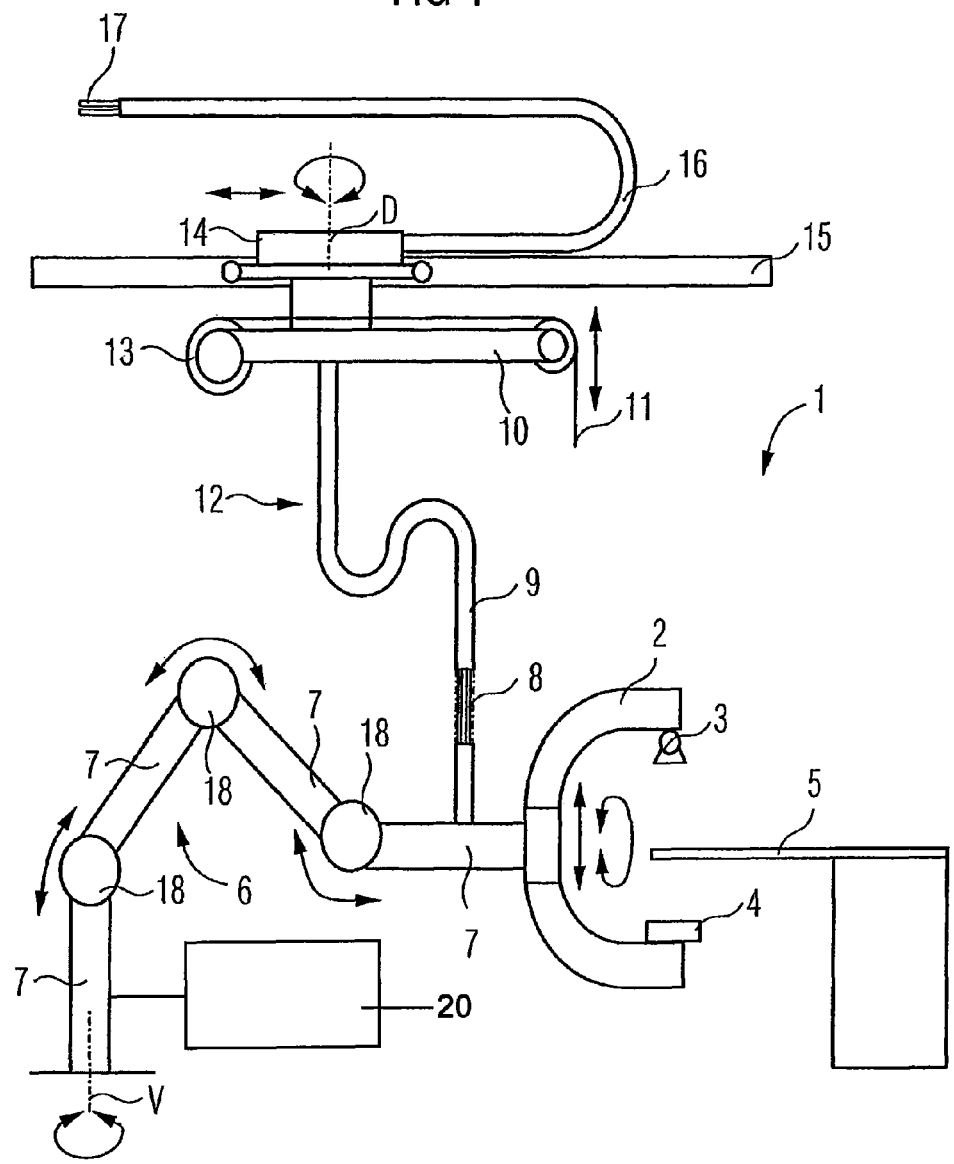
FIG. 1 illustrates one embodiment of a medical examination device.

FIG. 1 shows an exemplary medical examination device 1. The medical examination device 1 may include an x-ray device. The x-ray device may include a C-arm 2 with a radiation source 3 and a radiation detector 4 and a patient support couch 5, on which a patient is to be arranged for examination purposes. The C-arm 2 is arranged on a robot arm 6. The robot arm 6 may have several arm sections 7. The arm sections 7 may be connected to one another by different swivel joints 18. The robot arm 6 may be moveable in a rotational fashion about the vertical axis V, as shown by the double arrow. The C-arm 2, which is arranged on the robot arm 7, may be moveable along the arch shape, but can also be rotated in the longitudinal axis of the adjacent robot arm 7, as is shown by the respective movement arrows. The C-arm 2 may be moved by the robot arm 7. The robot arm 7 may be controlled by a control device 20, which controls the overall drive of the examination device, and consequently it is possible to move the robot arm 7 into different image recording positions.

This robot-controlled movement described by way of example here requires the majority of supply lines 8, which may be power or signal lines, but also lines with a hydraulic liquid or pneumatic lines, to be supplied from above (e.g., from the ceiling). The supply lines 8 are accommodated in a tube, shown here in partial cutout, predominantly a grooved tube 9. The grooved tube 9 and the supply lines 8 may be routed to a gallows 10, on which a cable pull 11 is arranged, by which the supply lines 8 and/or the grooved tube 9 plus the supply lines 8 are attached. A line reserve 12, such as a length storage unit, is thus formed, from which in the event of a movement of the C-arm 2 by the robot 6, the corresponding length can be adjusted. The supply lines 8 are connected as described to the robot arm 6 and/or the corresponding components, to which the supply lines 8 lead.

The gallows 10, on which a balancing weight 13 is arranged, is arranged on a carriage 14 and can be rotated about a vertical axis of rotation D relative hereto. The cable pull 11 may be moved with the rotation of the gallows 10, and therewith the line storage unit 12.

The carriage 14 may be moved horizontally on guide rails 15, which may be fixed to the ceiling, as shown by the arrow illustration. Feed lines 17, which are connected to the supply lines 8 on the carriage or gallows side, are routed to the carriage 14 by an energy chain 16. However, the supply lines 8 may be routed directly by the carriage 14 into the energy chain 16 and to be connected to the corresponding device equipment at the other end.

The energy chain 16 may allow a path equalization in the direction of movement of the carriage 14 on the guide rails 15.

The cable pull 11 may be disposed on a gallows 10, which can be rotated about a vertical axis D, the gallows 10 being arranged on a carriage 14 that can be moved along horizontally running guide rails 15. One benefit of this arrangement is that it permits an increased freedom of movement of the corresponding component of the x-ray device, since in each case it is ensured that the supply lines 8 and/or tube 9 is not arranged at any point in time in the movement range, since the free line length is always pulled upwards by the cable pull which engages with a corresponding longitudinal section with the supply lines 8 and/or tube 9. The line storage unit 12 is also carried along at the same time and may be kept sufficiently short. An uncontrolled impact of the supply lines 8 and/or tube 9 is avoided as far as possible.

Figure 2:
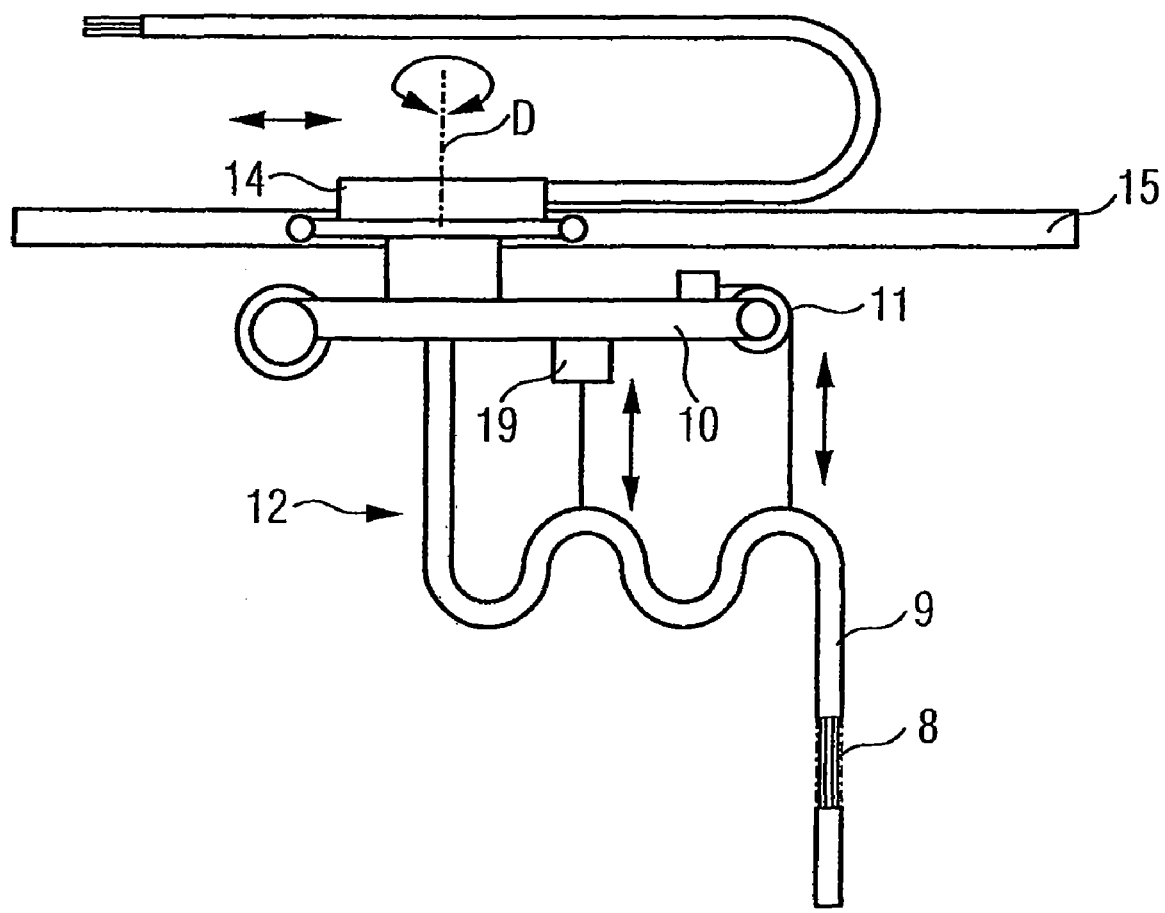
FIG. 2 illustrates another embodiment of a medical examination device.

In another embodiment, as shown in FIG. 2, a section from an additional x-ray device may be disposed in a region of the mounting of the supply lines 8 and/or tube 9 on the ceiling. The grooved tube 9 and the supply lines 8 may be attached to a cable pull 11 arranged on a gallows 10 on a longitudinal section. A second cable pull 19 may be provided on the gallows 10. The cable pull 10 may attach the tube 9 and the supply lines 8 from an additional longitudinal section. If an even larger line reserve 12 is needed, this can as a result also be embodied on the gallows so that it is possible to prevent the tube 9 and the supply lines 8 from hanging too low in the region of the line reserve. The line reserve 12, albeit larger than in the embodiment according to FIG. 1, is also carried along here at any point in time, since the gallows 10 is also arranged here on a carriage 14, which is horizontally moveable on the guide rails 15 and can be rotated about the rotational axis D.

Various embodiments described herein can be used alone or in combination with one another. The foregoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical examination device comprising:
 a gallows that is rotatably mounted on a rail-guide carriage; and
 a plurality of supply lines that supply a medical device, the plurality of supply lines being routed from above,
 wherein the plurality of supply lines is arranged on the rotatable gallows and extends from the rotatable gallows to the medical device, and
 wherein a longitudinal section of the plurality of supply lines is attached to at least one Bowden cable arranged on the rotatable gallows.

2. The examination device as claimed in claim 1, wherein the rail-guide carriage or the gallows is connected to an energy chain.

3. The examination device as claimed in claim 1, further comprising a balancing weight that is provided on the gallows.

4. The examination device as claimed in claim 1, further comprising a common tube, the plurality of supply lines being routed in or along the common tube, with which the Bowden cable engages.

5. The examination device as claimed in claim 1, wherein the Bowden cable is a cable pull.

6. The examination device as claimed in claim 1, wherein the medical device is an x-ray device.

7. The examination device as claimed in claim 6, wherein the plurality of supply lines supplies the x-ray device.

8. The examination device as claimed in claim 6, wherein the x-ray device includes: a C-arm with a radiation source and a radiation detector, and a patient support couch, on which a patient is to be arranged for examination purposes.

9. The examination device as claimed in claim 8, wherein the C-arm is arranged on a robot arm having several arm sections, the several arm sections being connected to one another by different swivel joints, such that the robot arm is moveable in a rotational fashion about a vertical axis.

10. The examination device as claimed in claim 9, wherein the C-arm is moveable along an arch shape and rotated about a longitudinal axis of the robot arm.

11. The examination device as claimed in claim 10, wherein the robot arm is controlled by a control device that controls the overall drive of the x-ray device and is operable to move the robot arm into different image recording positions.

12. The examination device as claimed in claim 11, wherein the plurality of supply lines supplies power to the control device and the x-ray device.

13. The examination device as claimed in claim 1, wherein the plurality of supply lines includes all of the supply lines.

* * * * *